United States Patent
Kreger et al.

(10) Patent No.: US 6,675,036 B2
(45) Date of Patent: Jan. 6, 2004

(54) DIAGNOSTIC DEVICE INCLUDING A METHOD AND APPARATUS FOR BIO-POTENTIAL NOISE CANCELLATION UTILIZING THE PATIENT'S RESPIRATORY SIGNAL

(75) Inventors: Kevin Scott Kreger, Milwaukee, WI (US); Bo Johan Pettersson, Wauwatosa, WI (US)

(73) Assignee: GE Medical Systems, Inc., Waukesha, WI (US)

(*) Notice: Subject to any disclaimer, the term of this patent is extended or adjusted under 35 U.S.C. 154(b) by 188 days.

(21) Appl. No.: 09/682,091

(22) Filed: Jul. 18, 2001

(65) Prior Publication Data

US 2003/0018248 A1 Jan. 23, 2003

(51) Int. Cl.[7] .................................................. A61B 5/05
(52) U.S. Cl. ....................................................... 600/413
(58) Field of Search ................................. 600/407, 410, 600/413, 419, 436, 428; 324/307, 368, 309, 322; 128/901

(56) References Cited

U.S. PATENT DOCUMENTS

| | | | |
|---|---|---|---|
| 4,537,196 A | | 8/1985 | Phillipps et al. |
| 4,710,717 A | * | 12/1987 | Pelc et al. ................... 324/309 |
| 4,781,201 A | | 11/1988 | Wright et al. |
| 4,991,587 A | * | 2/1991 | Blakeley et al. ............. 600/483 |
| 4,994,743 A | | 2/1991 | Glover et al. |
| 5,038,785 A | * | 8/1991 | Blakeley et al. ............. 600/484 |
| 5,188,116 A | | 2/1993 | Pommrehn et al. |
| 5,363,844 A | * | 11/1994 | Riederer et al. ............. 600/413 |
| 5,436,564 A | | 7/1995 | Kreger et al. |
| 5,490,516 A | | 2/1996 | Hutson |
| 5,503,160 A | | 4/1996 | Pering et al. |
| 5,529,068 A | * | 6/1996 | Hoenninger et al. ........ 600/413 |
| 5,794,623 A | | 8/1998 | Forbes |
| 5,800,354 A | | 9/1998 | Hofland et al. |
| 6,070,097 A | | 5/2000 | Kreger et al. |
| 6,132,381 A | | 10/2000 | Forbes et al. |
| 6,144,874 A | * | 11/2000 | Du ............................... 600/413 |
| 6,535,754 B2 | * | 3/2003 | Fishbein et al. ............. 600/422 |

* cited by examiner

Primary Examiner—Sang Y. Paik
Assistant Examiner—Daniel Robinson
(74) Attorney, Agent, or Firm—Michael Best & Friedrich LLP

(57) ABSTRACT

A diagnostic medical imaging device including a signal processor that includes an adaptive filter noise canceler that is used to reduce the additive electrical noise on low power bio-potential signals caused by a patient's respiration. A noise reference signal associated with the patient's respiration is adaptively filtered with only minimal time delay and subtracted from a noisy bio-potential signal that is acquired from the patient. The resultant signal is a clean bio-potential signal that may be used for, among other things, triggering an MRI scan. The noise reference signal is received by an adaptive filter having adjustable filter coefficients. The filter coefficients are adjusted using the clean bio-potential signal that acts an error signal.

28 Claims, 4 Drawing Sheets

DIAGNOSTIC DEVICE INCLUDING A METHOD AND APPARATUS FOR BIO-POTENTIAL NOISE CANCELLATION UTILIZING THE PATIENT'S RESPIRATORY SIGNAL

BACKGROUND OF INVENTION

The present invention relates to noise cancellation, and more particularly, to techniques for canceling noise in a bio-potential signal caused by a patient's respiration.

A bio-potential signal is any electrical signal measured from the human body. An array of sensors (also commonly called transducers) are typically connected to the patient to acquire measurements of such signals. Typical examples of bio-potential signals include an electrocardiogram (ECG), an electroencephalogram (EEG), and an electromyogram (EMG). An ECG (also known as EKG) is a record of the electrical activity of the heart as recorded by an electrocardiograph. An EEG is a record of the electrical activity of the brain as recorded by an electroencepalograph. An EMG is a record of the electrical activity of muscle as recorded by an electromyograph.

When a bio-potential signal is acquired from a patient, the measured signal typically is representative of not only the desired electrical activity, but also additive electrical noise introduced by other systems. Bio-potential signals are intrinsically of low power and hence susceptible to electrical interference. A patient's respiratory system is one example of a system that may introduce additive electrical noise. Respiration causes variability in bio-potential signals primarily due to the changes in the geometry of the chest and tilting of the heart during lung or pulmonary function. Electrical noise associated with the respiration of a patient can overlap or combine with the electrical activity of a bio-potential signal. The resultant acquired signal contains bio-potential signal content that is indistinguishable from the noise content.

When an acquired bio-potential signal includes electrical noise introduced by other systems, the acquired signal is known as a noisy bio-potential signal. Typically, in order for the noisy bio-potential signal to have medical significance it must be filtered to remove the additive electrical noise. A bio-potential signal that has been filtered is known as a clean bio-potential signal. Clean bio-potential signals have varying degrees of cleanliness depending upon what type of filtering is utilized. The type of filtering utilized often depends upon the end use of the clean bio-potential signal and the degree of accuracy required by that end use.

SUMMARY OF INVENTION

Monitoring devices generally have lower accuracy requirements than diagnostic devices. Monitoring devices can therefore use filters that are less expensive and less complex than the filters required on devices with higher accuracy requirements. An ECG monitor is one example of a monitoring device that uses analog and digital filtering technology to output a "clean" bio-potential signal. Although the output signal is adequate for the purposes of monitoring, the signal is largely time delayed and the signal invariably has an appreciable amount of the desired frequency content removed. This type of output is unacceptable for many diagnostic devices.

The diagnostic quality of a bio-potential signal may be reduced depending upon the frequency content removed and the amount of time delay introduced during filtering. Diagnostic applications typically require very accurate, minimally time delayed data. A magnetic resonance imaging (MRI) device is one example of a device that requires very accurate, minimally time delayed bio-potential signals that contain an appreciable amount of the desired frequency content. If the bio-potential signal is largely time delayed, or has an appreciable amount of the desired frequency content removed, the bio-potential signal may not be as useful as a diagnostic tool. The desired frequency content is all, and only all, of the frequency content of the signal of interest. The measured signal includes additional frequency content (i.e., frequency content due to noise) that is removed according to the invention leaving only the desired frequency content. Generally, analog and digital filters remove the additional frequency content and frequency content of the signal of interest, resulting in a signal that has reduced quality as a diagnostic tool.

Cardiac and cardiovascular imaging using MRI techniques is frequently utilized because of the advantages MRI has over other imaging techniques that typically employ radiation, such as X-rays. However, for cardiac studies, the subject is often required to remain within the MRI device for a duration of up to sixty minutes. Frequently, certain bio-potential signals, most notably the ECG signal, are measured during an MRI scan. Measurement of bio-potential signals may be required not only to monitor and diagnose the status of critically ill patients using various types of monitoring and diagnostic medical equipment, but measurement may also be required to synchronize the acquisition of MRI data with certain physiological phenomena such as the beating of the heart when using medical imaging devices. This synchronization is known as triggering. When an ECG signal is utilized, a threshold detector is set to output an actuation signal when the peak of the QRS complex is detected. When a noisy ECG signal is utilized, it is difficult to set the threshold at a level that will output an actuation signal for all (but only all) peaks of the QRS complexes. If the threshold is set too high it may cause peaks of the QRS complexes to be missed, if the threshold is set too low other parts of the ECG signal will be detected by the threshold detector and a false trigger may result. Another problem associated with attempting to trigger off a noisy ECG signal is the introduction of time-wise inaccuracies, or jitter, in the detection of the peaks of the QRS complexes.

Accordingly, the invention provides a diagnostic medical imaging device including an adaptive filter noise canceler to reduce the electrical noise associated with the patient's respiration and the like in low powered bio-potential signals. The adaptive filter noise canceler includes an adaptive filter unit having a noise reference input for receiving a noise reference signal associated with the patient's respiration, a clean bio-potential input for receiving a clean bio-potential signal, and a filtered noise reference output for outputting a filtered noise reference signal. The adaptive filter noise canceler also includes a summing node having a noisy bio-potential input for receiving a noisy bio-potential signal, a filtered noise reference input for receiving the filtered noise reference signal, and a clean bio-potential output for outputting the clean bio-potential signal. The adaptive filter noise canceler also includes a feed-back loop that electrically couples the clean bio-potential output and the clean bio-potential input, and a feed-forward loop that electrically couples the filtered noise reference output and the filtered noise reference input.

In one embodiment of the invention, the noise reference signal is produced from the electrical signal generated by a bellows transducer connected to the patient's chest. The electrical signal corresponds to the extension or deflection of the patient's chest and therefore is associated with the patients respiration.

In another embodiment of the invention, the noise reference signal is produced from the electrical signal generated by an array of sensors connected to the patient using a number of generally known methods to measure the electrical noise caused by the patient's respiration (e.g., transthoracic impedance). The electrical noised is caused by the patient's respiration and is therefore inherently associated with the patients respiration.

It is an advantage of the invention to permit the continuous acquisition of low power bio-potential signals in the presence of varying values of electrical noise associated with the patient's respiration. The subtraction of a filtered noise reference signal from the noisy bio-potential signal effectively reduces the additive electrical noise associated with the patient's respiration and produces the clean bio-potential signal. The continuous adjustment of filter coefficients for the adaptive filter unit accommodates changes in the value of electrical noise associated with the patient's respiration.

The electrical noise associated with the patient's respiration is removed from the noisy bio-potential signal with only minimal alteration of the desired frequency content of the bio-potential signal. Additionally, the additive electrical noise associated with the patient's respiration is removed with only minimal time delay to allow for the use of the clean bio-potential signal for, among other things, triggering diagnostic medical imaging devices such as an MRI.

These features as well as other advantages of the invention will become apparent upon consideration of the following detailed description and accompanying drawings of the embodiments of the invention described below.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of including and comprising and variations thereof herein is meant to encompass the items listed thereafter and equivalents thereof as well as additional items.

Figure 1:
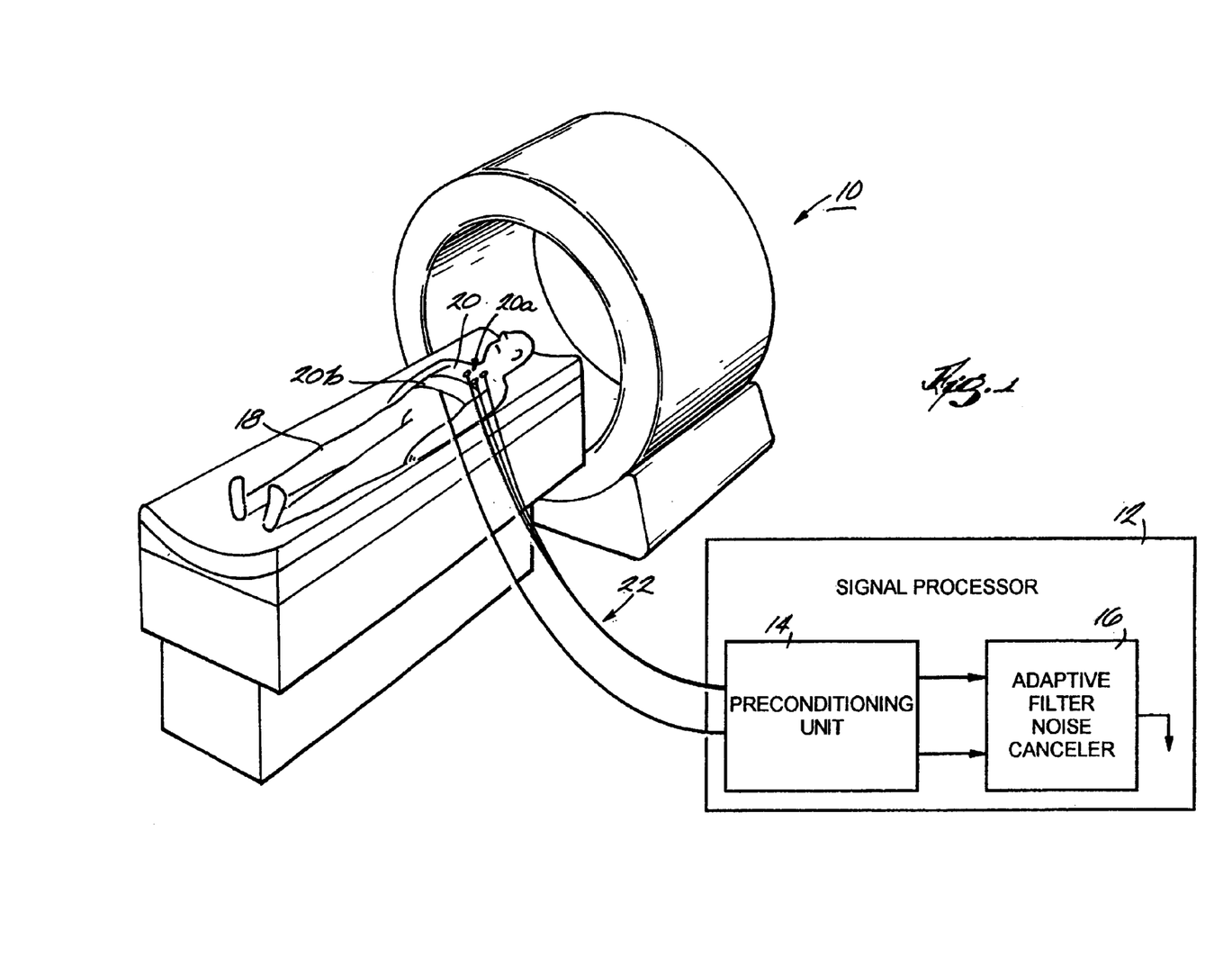
FIG. 1 is an illustration of an MRI device embodying the invention.
Figure 2:
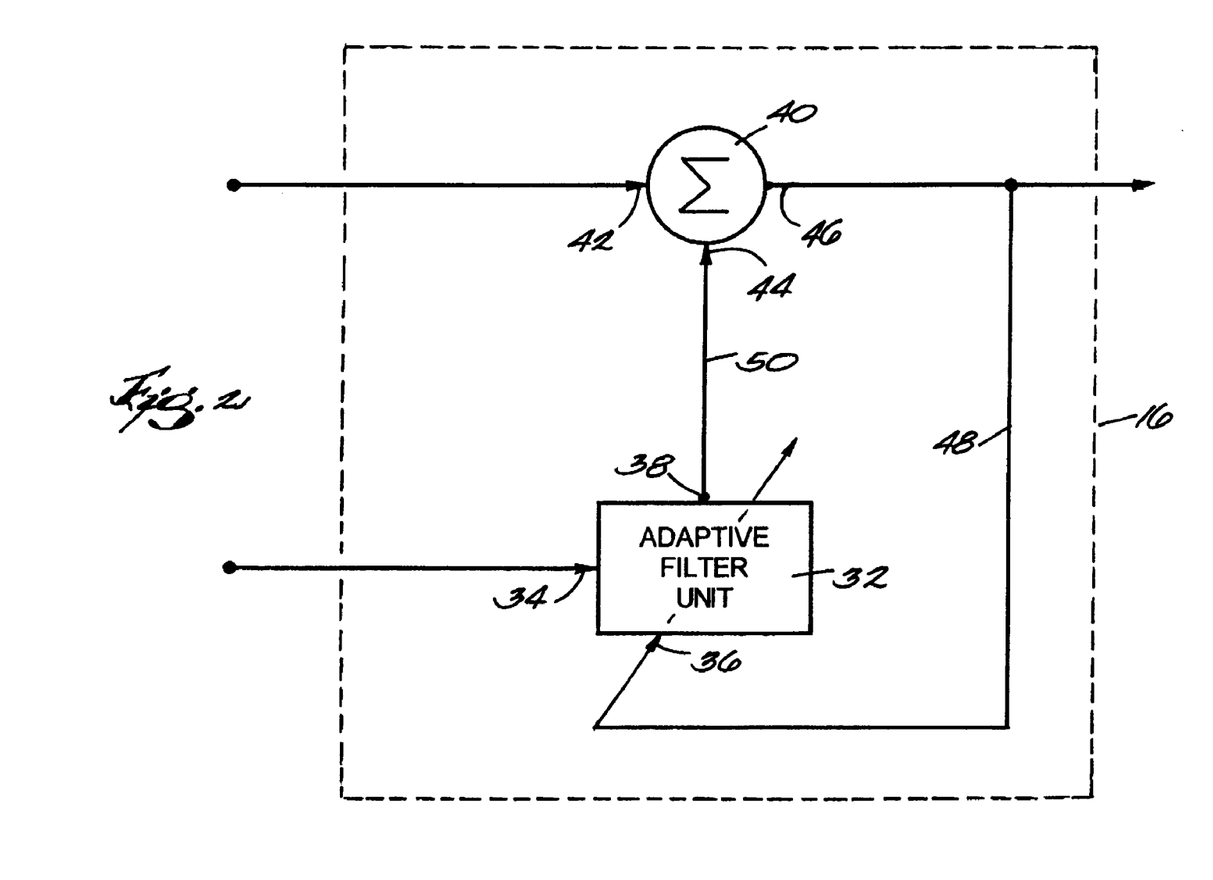
FIG. 2 is a schematic illustration of an adaptive filter noise canceler for the MRI device illustrated in FIG. 1.

FIG. 1 illustrates an MRI device 10 embodying the invention. The MRI device 10 is similar to those generally known in the art. The MRI device 10 includes a signal processor 12 having a preconditioning unit 14 and an adaptive filter noise canceler 16 connected thereto. A patient 18 is connected to an array of transducers 20 (including 20a and 20b) that are electrically connected to the preconditioning unit 14 of the signal processor 12 by flexible leads 22. The signals acquired from the patient using the transducers 20 may be preconditioned using any generally known techniques. The preconditioning unit 14 may include, among other things, an amplifier (not shown) to adjust the amplitude of the signals to magnitudes appropriate for use, a filter (not shown) to eliminate noise signals outside the bandwidth of the acquired signals, and a high speed A/D converter (not shown) to provide digital signals for input to the adaptive filter noise canceler 16. As shown in FIG. 2, the adaptive filter noise canceler 16 includes an adaptive filter unit 32 having a noise reference input 34 for receiving a noise reference signal NR associated with the patient's 18 respiration, a clean bio-potential input 36 for receiving a clean bio-potential signal CB, and a filtered noise reference output 38 for outputting the filtered noise reference signal FNR. The adaptive filter noise canceler 16 also includes a summing node 40 having a noisy bio-potential input 42 for receiving a noisy bio-potential signal NB, a filtered noise reference input 44 for receiving the filtered noise reference signal FNR, and a clean bio-potential output 46 for outputting the clean bio-potential signal CB. The adaptive filter noise canceler 16 also includes a feed-back loop 48 that electrically couples the clean bio-potential output 46 and the clean bio-potential input 36, and a feed-forward loop 50 that electrically couples the filtered noise reference output 38 and the filtered noise reference input 44.

Figure 3:
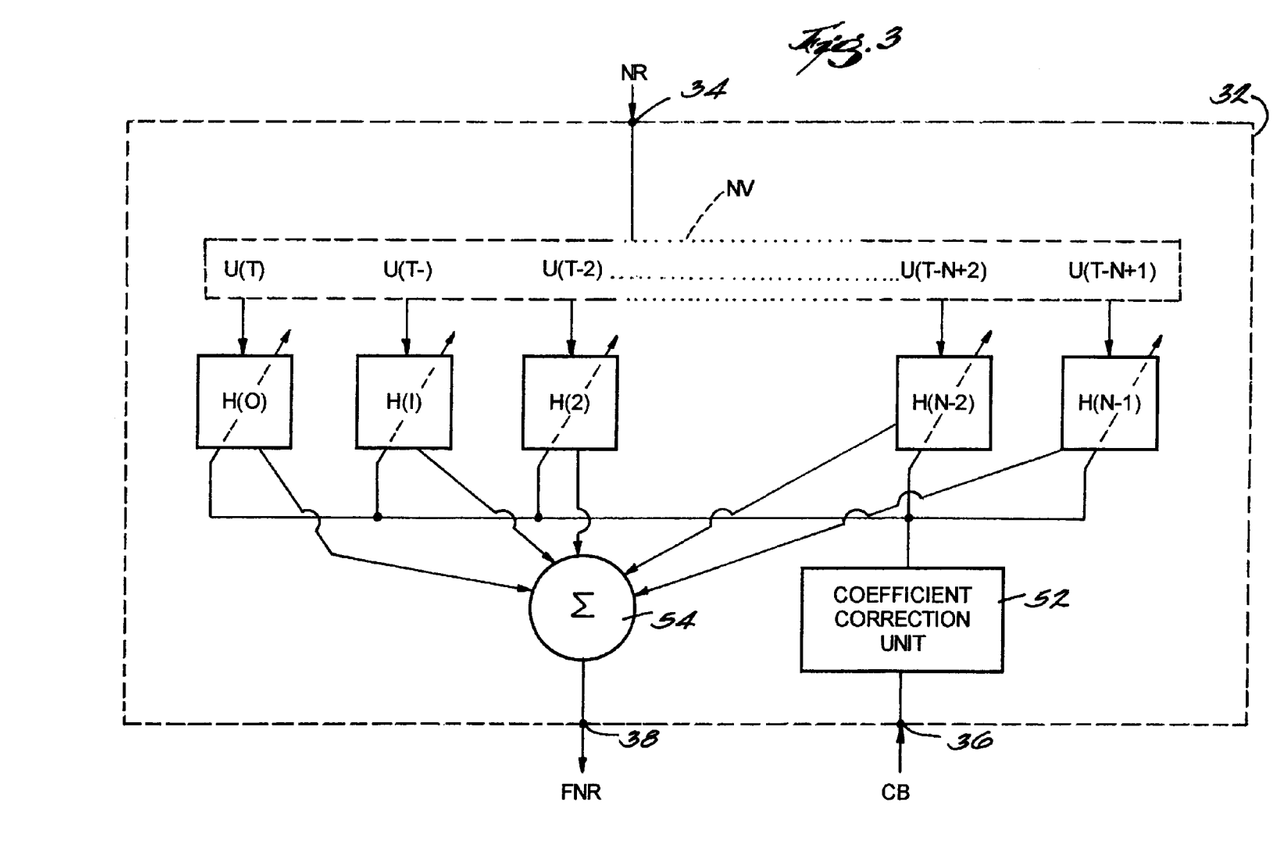
FIG. 3 is a schematic illustration of an adaptive filter unit in the adaptive filter noise canceler shown in FIG. 2.

The adaptive filter unit 32 is further illustrated in FIG. 3. The adaptive filter unit 32 modifies the noise reference signal NR associated with the patient's 18 respiration so that it matches an additive electrical noise AEN component of the noisy bio-potential signal NB caused by the patient's 18 respiration. The noisy bio-potential signal NB includes the summation of the clean bio-potential signal CB and the additive electrical noise AEN that is overlapped or combed with the clean bio-potential signal CB. The noise reference signal NR is typically modified by adjusting the amplitude and time delaying the signal to synchronize it with the noisy bio-potential signal NB. The noise reference signal NR is generally out of phase with the noisy bio-potential signal NB because the noise reference signal NR is measured with a transducer 20a located in a different location than the location where a transducer 20b used to measure the noisy bio-potential signal NB is located. Placement of the transducers 20 on the patient 18 in different locations leads to different times of propagation for the signals and therefore the measured signals are out of phase with respect to each other. Similarly, measurement of the noise reference signal NR results in the amplitude of the noise reference signal NR generally requiring adjustment of the amplitude to match it to the additive electrical noise AEN component of the noisy bio-potential signal NB.

The adaptive filter unit 32 has filter coefficients H(N), where N ranges from 0 to N−1, that are continually adjusted by a coefficient correction unit 52 that is electrically coupled to the clean bio-potential input 36. The clean bio-potential signal CB is utilized to adjust the filter coefficients H(N) for the next sample of the noise reference signal NR. The continuous adjustment of the filter coefficients H(N) accommodates changes in the value of the additive electrical noise AEN present in the noisy bio-potential signal NB. The filter coefficients H(N) are also adjusted so as to minimize any noise in the filtered noise reference signal FNR associated with the adaptive filter unit 32. The filtered noise reference signal FNR preferably is substantially similar to the additive electrical noise AEN component of the noisy bio-potential signal NB (i.e., the additive electrical noise AEN is the additional frequency content of the measured noisy bio-potential signal NB that is removed to obtain only the desired frequency content).

In one embodiment of the present invention, the adaptive filter unit 32 compiles a noise vector NV comprised of a current sample U(T) of the noise reference signal NR and N−1 previous samples of the noise reference signal NR taken at intervals dictated by the Nyquist sampling theorem. Each sample is designated U(T−N) where N ranges from 0 to N−1, therefore, the current sample is designated U(T) and the oldest sample in use is designated U(T−N+1). With each new sample U(T), the oldest sample is discarded so that the noise vector comprises the most recent N samples on a rolling basis. Each new sample U(T) is input into the adaptive filter unit 32 at the noise reference input 34. In the present embodiment, the noise reference signal NR is sampled at Hz by the high speed A/D converter (not shown) and the number of samples, N, is equal to 64. The noisy bio-potential signal NB is similarly sampled. As will be apparent from this description to one of ordinary skill in the art, other sampling rates and numbers of samples may be used subject to the general guidelines that more samples and a higher sampling frequency will provide better filtering and more accurate representation of the signal but will require faster processing hardware.

Each of the samples of the noise vector NV is weighted by a filter coefficient designated H(N) where N ranges from 0 to N−1 (N corresponds to the N samples of the noise vector NV). Some samples are weighted more heavily than other samples. The weighting process multiplies each sample U(T−N) of the noise vector NV by a corresponding filter coefficient H(N). The results of these multiplications are summed, as indicated by the summing node 54, to produce the filtered noise reference signal FNR that is output from the adaptive filter unit 32 at the filtered noise reference output 38.

The adaptive filter unit 32 described above is just one example of adaptive filtering technology that can be used to modify the noise reference signal NR to produce the filtered noise reference signal FNR that is substantially similar to the additive electrical noise AEN component of the noisy bio-potential signal NB. Any of the commonly known types of adaptive filters, including but not limited to finite impulse response (e.g., least mean square and recursive least square), infinite impulse response, and adaptive lattice filters may be used. The most important aspect of the adaptive filtering technology utilized is that it filters with only minimal time delay and does not remove an appreciable amount of the desired frequency content of the signal.

In operation, the patient 18 is connected to the array of transducers 20 that is connected to the patient 18 to acquire measurements of the noisy bio-potential signal NB and the noise reference signal NR. The transducers 20a, such as electrodes, may be utilized to measure the noisy bio-potential signal NB. In a preferred embodiment, the transducers 20a measure a noisy ECG using commonly practiced techniques. Also in a preferred embodiment, the transducer 20b, such as a bellows, may be utilized to measure the extension or deflection of the chest wall and to produce the noise reference signal NR associated with the patient's 18 respiration. Other commonly known methods of measuring electrical noise caused by the patient's 18 respiration may be used, although in the preferred embodiment of an MRI device 10, it is desirable to use mechanical type transducers 20 to measure the noise reference signal NR. The noisy bio-potential signal NB and the noise reference signal NR acquired from the patient 18 may be preconditioned in the preconditioning unit 14, as discussed above, before they are fed into the noisy bio-potential input 42 and the noise reference input 34.

Figure 4:
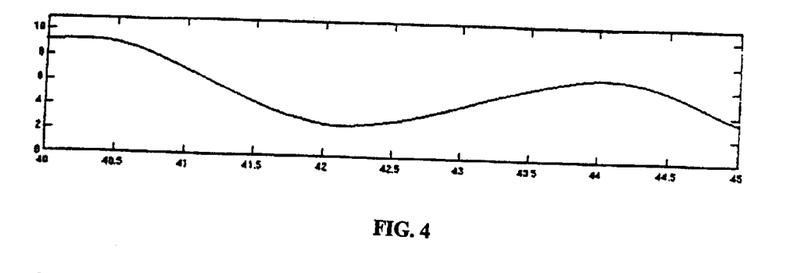
FIG. 4 is a graphical illustration of a noise reference signal associated with a patient's respiration.
Figure 5:
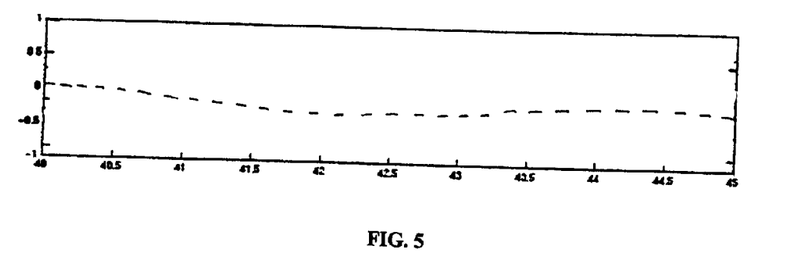
FIG. 5 is a graphical illustration of a filtered noise reference signal of FIG. 4.
Figure 6:
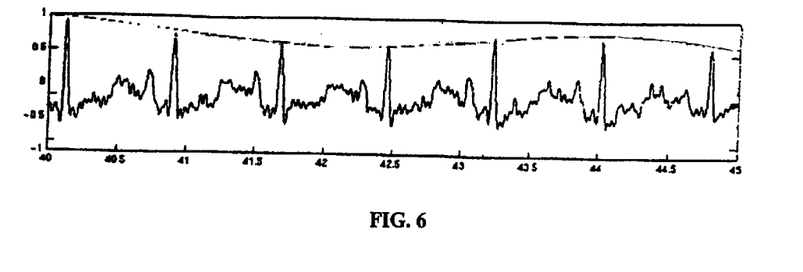
FIG. 6 is a graphical illustration of the noisy bio-potential (ECG) signal before noise cancellation.

The noise reference signal NR graphically illustrated in FIG. 4 is fed into noise reference input 34 of the adaptive filter unit 32. The current sample of the noise reference signal NR becomes sample U(T) of the noise vector NV and all previous samples are shifted one location to the right (as illustrated in FIG. 3) with the oldest sample no longer being used. Each filter coefficient H(N) is adjusted by the coefficient correction unit 52 according to the clean bio-potential signal CB that was simultaneously acquired with the previous sample U(T−1) of the noise reference signal NR. The samples U(T−N) of the noise vector NV are multiplied by the corresponding weighted filter coefficient H(N) of the adaptive filter unit 32. The results of these multiplications are summed using summing node 54. The summing node 54 may be either a circuit-based node or a software based node. The summing node 54 outputs the filtered noise reference signal FNR. FIG. 5 is a graphical illustration of a filtered noise reference signal FNR. As illustrated, the filtered noise reference signal FNR is in phase with the noisy bio-potential signal NB graphically illustrated in FIG. 6. The filtered noise reference signal FNR has a varying magnitude that corresponds to the changing value of electrical noise caused by the patient's 18 respiration as measured by the transducers 20a. It is this varying magnitude that causes the amplitudes of the peaks of the QRS complexes to vary, and thereby make setting a threshold level to trigger off the peaks of the QRS complexes difficult. The dotted line of FIG. 6 illustrates that the variation in amplitudes of the peaks of the QRS complexes is directly related to the additive electrical noise AEN. Note that some amplitudes are larger than they should be and some amplitudes are smaller than they should be.

The noisy bio-potential signal NB is fed into the noisy bio-potential input 42 of the adaptive filter noise canceler 16. The summing node 40 may be either a circuit-based node or a software based node. The summing node 40 produces the clean bio-potential signal CB by subtracting the magnitude of the filtered noise reference signal FNR from the magnitude of the noisy bio-potential signal NB. Because the filtered noise reference signal FNR is substantially similar to the additive electrical noise AEN component of the noisy bio-potential signal NB, the resultant signal is the clean bio-potential signal, or the bio-potential signal actually produced by the system of interest (e.g., the heart) without noise caused by the patient's 18 respiration (other types of additive noise may still be present in the clean bio-potential signal CB). The output of the summing node 40 is the output from the adaptive noise canceler 16. The output is the clean bio-potential signal CB. As discussed above, the clean bio-potential signal CB is also utilized by the coefficient correction unit 52 as an error signal to correct the filter coefficients H(N) of the adaptive filer unit 32. The clean bio-potential signal CB (error signal) is fed through the feed-back loop 48 to the clean bio-potential input 36 of the adaptive filter unit 32.

Figure 7:
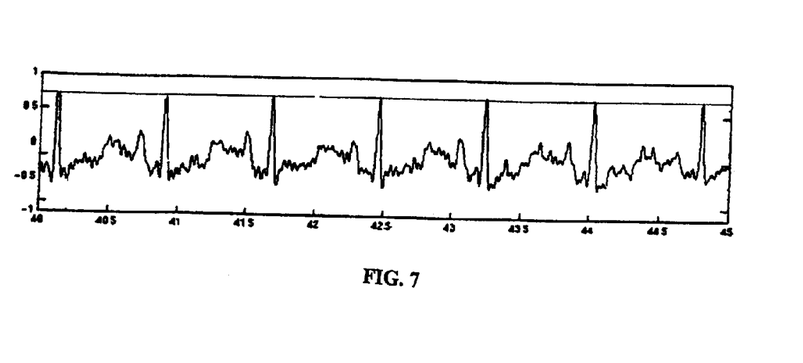
FIG. 7 is a graphical illustration of the clean bio-potential (ECG) signal after noise cancellation.

The clean bio-potential signal CB that is the output of the adaptive filter noise canceler 16 may be utilized to trigger a diagnostic medical imaging device. In a preferred embodiment, the diagnostic medical imaging device is an MRI device 10. However, other modalities of diagnostic medical imaging devices that require accurate minimal time delay clean bio-potential signals CB may equally benefit from use of the adaptive filter noise canceler 16. The clean bio-potential signal CB illustrated graphically in FIG. 7 has QRS complexes with peaks having constant amplitudes. It is much easier to establish a threshold level that triggers on all (but only all) peaks of the QRS complexes when the amplitudes all have the same magnitude.

The use of filtering technology that modifies the clean bio-potential signal CB by introducing a larger time delay or by removing an appreciable amount of the desired frequency content is not desirable for use in diagnostic medical imaging devices such as MRI devices 10. Introduction of a larger time delay results in the acquisition of an image that is delayed in time relative to the actual physical event generating the bio-potential signal. When the clean bio-potential signal CB is time delayed, the triggering off the clean bio-potential signal CB is time delayed and therefore the acquisition of the image is delayed and uncertainty of the trigger (i.e., jitter) may result. For diagnostic applications it is desirable to have all data acquired (image, bio-potential signal, etc.) synchronized so the physician analyzing the data is able to accurately interpret the physical event of interest. Removal of an appreciable amount of the desired frequency content from a clean bio-potential signal CB may result in missed triggers when the diagnostic medical imaging device is triggering off the clean bio-potential signal CB. Missed triggers similarly result in a decreased ability of the physician analyzing the data representing the physical event of interest to accurately diagnose the patient's problem and a loss in image quality. In a preferred embodiment, the clean bio-potential signal CB includes as much of the desired frequency content, and is as close to being delivered in real-time as adaptive filtering technology allows.

Various features and advantages of the invention are set forth in the following claims.

What is claimed is:

1. A diagnostic medical imaging device including a signal processor for removing additive electrical noise caused by a patient's respiration from a noisy bio-potential signal, the diagnostic medical imaging device comprising:

an adaptive filter unit having a noise reference input for receiving a noise reference signal associated with the patient's respiration, a clean bio-potential input for receiving a clean bio-potential signal, and a filtered noise reference output for outputting a filtered noise reference signal;

a summing node having a noisy bio-potential input for receiving the noisy bio-potential signal, a filtered noise reference input for receiving the filtered noise reference signal, and a clean bio-potential output for outputting the clean bio-potential signal;

a feed-back loop that electrically couples the clean bio-potential output and the clean bio-potential input; and a feed-forward loop that electrically couples the filtered noise reference output and the input for receiving the filtered noise reference signal.

2. The diagnostic medical imaging device of claim 1 wherein the diagnostic medical imaging device is an MRI device.

3. The diagnostic medical imaging device of claim 1 wherein the adaptive filter unit further includes adjustable filter coefficients.

4. The diagnostic medical imaging device of claim 3 wherein the adaptive filter unit further includes a coefficient correction unit electrically coupled to the clean bio-potential input, and wherein the coefficient correction unit adjusts the filter coefficients using the clean bio-potential signal.

5. The diagnostic medical imaging device of claim 1 wherein the content of the filtered noise reference signal is substantially similar to the additive electrical noise.

6. The diagnostic medical imaging device of claim 1 wherein the summing node subtracts the magnitude of the filtered noise reference signal from the magnitude of the noisy bio-potential signal.

7. The diagnostic medical imaging device of claim 1 wherein the adaptive filter unit is an infinite impulse response adaptive filter.

8. The diagnostic medical imaging device of claim 1 wherein the adaptive filter unit is a finite impulse response adaptive filter.

9. The diagnostic medical imaging device of claim 8 wherein the finite impulse response adaptive filter is a least mean square finite impulse response adaptive filter.

10. The diagnostic medical imaging device of claim 8 wherein the finite impulse response adaptive filter is a recursive least square finite impulse response adaptive filter.

11. The diagnostic medical imaging device of claim 1 wherein the signal processor utilizes the clean bio-potential signal to trigger an acquisition of an image byte diagnostic medical imaging device.

12. In a diagnostic medical imaging device, a method of removing an additive electrical noise component of a noisy bio-potential signal caused by a patient's respiration from the noisy bio-potential signal, the method comprising the steps of:

sampling the noisy bio-potential signal;

sampling a noise reference signal associated with the patient's respiration;

filtering the noise reference signal with only minimal time delay to produce a filtered noise reference signal;

subtracting the magnitude of filtered noise reference signal from the magnitude of the noisy bio-potential signal;

outputting a clean bio-potential signal; and triggering the diagnostic medical imaging device on the clean bio-potential signal to generate an image.

13. The method of claim 12 wherein the subtracting act includes the filtered noise reference signal having content substantially similar to the additive electrical noise.

14. The method of claim 12 wherein the filtering act comprises time delaying the noise reference signal to synchronize the noise reference signal and the noisy bio-potential signal.

15. The method of claim 12 further comprising the act of preconditioning the noise reference signal, wherein the preconditioning act includes matching the amplitude of the noise reference signal to the amplitude of the additive electrical noise.

16. The method of claim 12 wherein the filtering act further comprises the act of adjusting filter coefficients using the clean bio-potential signal.

17. The method of claim 12 wherein the sampling of the noise reference signal act comprises attaching a mechanical type transducer to the patient's chest to measure the noise reference signal.

18. The method of claim 17 wherein the mechanical type transducer is a bellows.

19. A signal processor for removing electrical noise caused by a patient's respiration from a noisy bio-potential signal, the signal processor comprising:

an adaptive filter unit having a noise reference input for receiving a noise reference signal associated with the patient's respiration, a clean bio-potential input for receiving a clean bio-potential signal, and a filtered noise reference output for outputting a filtered noise reference signal;

a summing node having a noisy bio-potential input for receiving the noisy bio-potential signal, a filtered noise reference input for receiving the filtered noise reference signal, and a clean bio-potential output for outputting the clean bio-potential signal;

a feed-back loop that electrically couples the clean bio-potential output and the clean bio-potential input; and a feed-forward loop that electrically couples the filtered noise reference output and the input for receiving the filtered noise reference signal.

20. The signal processor of claim 19 wherein the adaptive filter unit further includes adjustable filter coefficients.

21. The signal processor of claim 20 wherein the adaptive filter unit further includes a coefficient connection unit electrically coupled to the clean bio-potential input, and wherein the coefficient correction unit adjusts the filter coefficients using the clean bio-potential signal.

22. The signal processor of claim 19 wherein the content of the filtered noise reference signal is substantially similar to the additive electrical noise.

23. The signal processor of claim 19 wherein the summing node subtracts the magnitude of the filtered noise reference signal from the magnitude of the noisy bio-potential signal.

24. The signal processor of claim 19 wherein the adaptive filter unit is an infinite impulse response adaptive filter.

25. The signal processor of claim 19 wherein the adaptive filter unit is a finite impulse response adaptive filter.

26. The signal processor of claim 25 wherein the finite impulse response adaptive filter is a least mean square finite impulse response adaptive filter.

27. The signal processor of claim 25 wherein the finite impulse response adaptive filter is a recursive least square finite impulse response adaptive filter.

28. The signal processor of claim 19 wherein the signal processor is coupled to a diagnostic medical imaging device, wherein the signal processor utilizes the clean bio-potential signal to trigger an acquisition of an image by the diagnostic medical imaging device.

* * * * *

UNITED STATES PATENT AND TRADEMARK OFFICE
CERTIFICATE OF CORRECTION

PATENT NO.   : 6,675,036 B2                                              Page 1 of 1
DATED        : January 6, 2004
INVENTOR(S)  : Kevin Scott Kreger and Bo Johan Pettersson It is certified that error appears in the above-identified patent and that said Letters Patent is hereby corrected as shown below:

Column 9,
Line 21, delete the word "connection" and replace with the word -- correction --

Signed and Sealed this

Sixth Day of April, 2004

JON W. DUDAS
*Acting Director of the United States Patent and Trademark Office*